United States Patent [19]

Bohn et al.

[11] Patent Number: 4,458,020

[45] Date of Patent: Jul. 3, 1984

[54] INTEGRATED SINGLE TUBE PLUNGER IMMUNOASSAY SYSTEM HAVING PLURAL REAGENT CHAMBERS

[75] Inventors: Joseph W. Bohn; Peter A. Cohen, both of San Diego; Bruce L. Zuraw, Del Mar, all of Calif.

[73] Assignee: Quidel, La Jolla, Calif.

[21] Appl. No.: 441,605

[22] Filed: Nov. 15, 1982

[51] Int. Cl.³ .................. G01N 33/54; G01N 33/58
[52] U.S. Cl. ......................... 435/296; 210/927; 210/DIG. 24; 422/61; 435/287; 435/300; 436/808; 436/810
[58] Field of Search ............... 435/296, 300; 210/927, 210/DIG. 24; 422/61; 436/808, 810

[56] References Cited

U.S. PATENT DOCUMENTS

| | | | |
|---|---|---|---|
| 3,355,098 | 11/1967 | Farr | 210/927 X |
| 3,481,477 | 12/1969 | Farr | 210/927 X |
| 3,493,503 | 2/1970 | Mass | 210/927 X |
| 3,512,940 | 5/1970 | Shapiro | 210/927 X |
| 3,702,806 | 11/1972 | Oliva | 435/300 |
| 3,802,843 | 4/1974 | Kim | 210/927 X |
| 3,832,141 | 8/1974 | Haldopoulos | 210/927 X |
| 3,849,256 | 11/1974 | Linder | 435/300 X |
| 3,870,639 | 3/1975 | Moore | 210/927 X |
| 3,954,614 | 5/1976 | Wright | 210/927 X |
| 3,954,623 | 5/1976 | Hammer | 210/927 X |
| 3,955,423 | 5/1976 | Ohringer | 210/927 X |
| 3,969,250 | 7/1976 | Farr | 210/927 X |
| 4,057,499 | 11/1977 | Buono | 210/927 X |
| 4,135,884 | 1/1979 | Shen | 435/296 X |
| 4,197,287 | 4/1980 | Piasio | 435/296 X |
| 4,424,279 | 1/1984 | Bohn | 436/810 X |

Primary Examiner—Sidney Marantz
Attorney, Agent, or Firm—Hubbard & Stetina

[57] ABSTRACT

A system for conducting an immunoassay in a single chamber, by concentrating antibodies for antigenic components on microbeads treated for binding immunological components, physically separating the fluid from which the immunological active component is separated, and determining the amount of immunological component collected on the beads, comprising a multiple-chamber dispensing cylinder.

7 Claims, 3 Drawing Figures

INTEGRATED SINGLE TUBE PLUNGER IMMUNOASSAY SYSTEM HAVING PLURAL REAGENT CHAMBERS

TECHNICAL FIELD

This invention relates to immunological methods and apparatus. More specifically, this invention relates to a specific technique and apparatus for conducting an immunological assay procedure upon a fluid, such as a body fluid, or a carrier fluid, in which the immunological component to be detected is carried.

BACKGROUND OF THE INVENTION

With the advances in immunochemistry, there has been an increasing and recently accelerated need for more efficient and less expensive methods and techniques for conducting immunoassays. In many fields of endeavor in molecular biology, biochemistry, biology and genetics, it is necessary to conduct hundreds or even thousands of immunological assay procedures in order to accomplish a single result.

In the clinical treatment of immunological diseases and disorders, it is very desirable to conduct any necessary immunological assays quickly, inexpensively and efficiently in order that the time of the patient and the physician may not be wasted by long delays and repeated visits. There is, accordingly, a long-felt need for more accurate, less expensive, simpler and more efficient immunological assay procedures and apparatus for use in the physician's office or in the clinical laboratory. A large number of immunological detector mechanisms, techniques and materials have been developed over the past decade. The now classical radioimmunoassay technique is still very widely used, though it is being replaced with other techniques which use non-radioactive indicators. Enzyme linked immunoassay techniques, for example, and other photometric, fluorophotometric and colorimetric methods are also applicable to particular species of immunological components. While these advances have made the relatively rapid and accurate assay of antigens and antibodies quite feasible, the need for still more accurate, and simultaneous inexpensive and efficient apparatus and methods has gone unfilled, both in the research laboratory and in the clinical laboratory.

Existing immunoassay technologies are frequently so complicated or time-consuming that a technician is able to run only a very limited number of assays per day. On the other hand, in a clinical laboratory, as an example, the number of assays to be run during a particular day may not justify setting up and operating the apparatus for conducting the assay. Sometimes, in such circumstances, technicians allow patient samples to accumulate until there are enough samples to justify the labor of running the assay. In many clinical situations, such as in the instance of a suspected heart attack, it is distinctly detrimental to the patient if there are any delays or any inconveniences intrinsic in the assay technology. Rapid and accurate assays in such instances are vital to the health of the patient.

This invention comprises a system which overcomes, fully or in large extent, all of the foregoing disadvantages of the prior art.

SUMMARY OF THE INVENTION

According to this invention, a fluid which contains the immunological constituent of interest, e.g. an antigen, is introduced into a plunger filter apparatus, typically though not necessarily through the filter, and into contact with immunologically binding beads which are in the plunger filter. These immunologically binding beads bind to the immunological constituent of interest, e.g. the antigen or antibody, and extract it from the solution in which it is carried. The solution is then forced to flow out of the plunger filter, through the filter, leaving the beads in the plunger filter. The beads are washed to remove excess fluid and to retain only the immunological constituent of interest which is bound to the beads. A developer is introduced into the plunger filter which binds to the immunological constituent of interest, e.g. the antigen or antibody. Excess developer may be removed by washing, filtration, etc. Finally, the immunological constituent of interest is determined by measuring the developer according to the indicator which characterizes the developer. All of these operations are carried out in a single-unit system in which the necessary reagents are contained in respective reagent chambers.

As an apparatus, the invention comprises a novel improved plunger filter assembly containing beads which bind selected immunologically active constituents of the fluid to be tested, a container tube in which the plunger filter fits in a movable, fluid-tight relationship to permit fluid to be forced through the filter in either direction, the plunger filter assembly comprising a plurality of reagent chambers, each containing a predetermined reagent or wash solution.

In a more specific and non-limiting sense the invention may be described as an immunoassay system comprising a cylindrical container tube having an open end and a closed end, and a plunger filter assembly received in the open end of the container tube and being slidable in the container tube, the plunger filter assembly comprising a cylindrical reaction tube, a movable seal fixedly secured at the proximal end of the cylindrical tube, the distal end extending outwardly toward the open end of the container tube comprising multiple-reagent chambers for selective communication with the reaction tube, the seal being movable with respect to the interior walls of the container tube and forming a substantially fluid-tight movable seal between the proximal end of the plunger filter and the container tube, a high surface area, typically dome-shaped filter inside and closing the proximal end of the plunger filter cylinder to the passage of material in and out of said proximal end except for fluids and particles which can pass through the filter, and immunologically reactive beads which, in use, bind selected immunologically active constituents of the fluid to be assayed, the immunologically active beads having porous surfaces treated with an immunologically active constituent and being too large to pass through the filter.

A preferred form, the filter includes pores as large as possible to permit free two-way passage of the assayed fluid and its constituents, such as blood cells, while still being small enough pored to retain the beads on one side of the filter without clogging; the filter seal comprises a skirt extending circumferentially.

Again in the preferred form, the immunologically active beads are large enough overall diameter not to pass or clog the filter, but otherwise as small as possible to slow their rate of settling, thus speeding the assay reactions. In addition, the beads should be small enough pored to prevent any antibody or developing agent from entering the interior of the beads; in this way, all coupling and reaction steps occur on the outer surface of the beads, speeding reaction time and decreasing background interference. Within this pore size constraint, the bead pore size should still be maximal to decrease the specific gravity of the beads, hence slow the rate of bead settling and further speed assay reaction times.

DESCRIPTION OF THE BEST MODE

In the following description, the apparatus and the method will be described, in exemplary terms only, for an antigen-determining immunoassay test. This discussion, however, is simply to illustrate the structure and use of the apparatus and the technique and steps of the method. Parallel steps and uses of the apparatus would be involved in any immunological component determination using the particular developer of choice for that particular immunological assay. For example, a bound enzyme detection technique will be described. Clearly, immunofluorescent, RIA and other techniques, as well as ELISA techniques, may be used. The best mode, as described hereinafter, is, accordingly, to be considered exemplary and not limiting as to the scope and concept of the invention.

Figure 1:
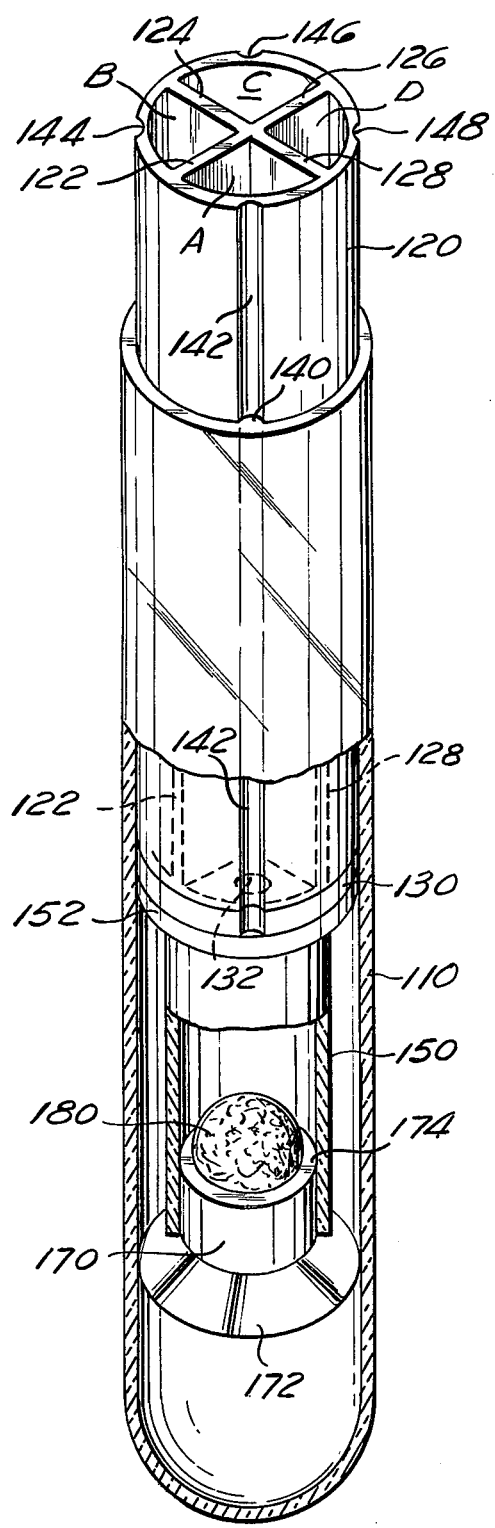
FIG. 1 is a perspective view of the basic structure of the system and apparatus of this invention.

Referring first to FIG. 1, for a general depiction of the apparatus, the inventive system and apparatus comprises a container tube 110 which typically is in the form of a conventional cylindrical tube, often referred to as a test tube.

The reagent chamber assembly comprises a cylindrical tube 120 which is configured and constructed to be adapted to fit within the cylindrical portion of tube 110. Walls 122, 124, 126 and 128 divide reagent chamber assembly into a plurality of chambers, in exemplary embodiment there being four such chambers denominated by A, B, C and D.

Figure 3:
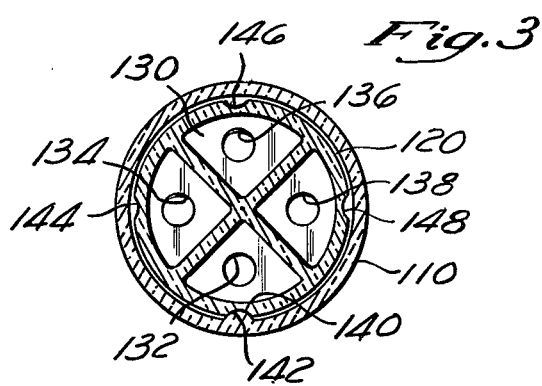
FIG. 3 is a lateral cross-section of the apparatus as shown in FIG. 2 taken along lines 3—3 as shown in the direction of the arrows, showing the communication ports in the reagent chambers.
Figure 2:
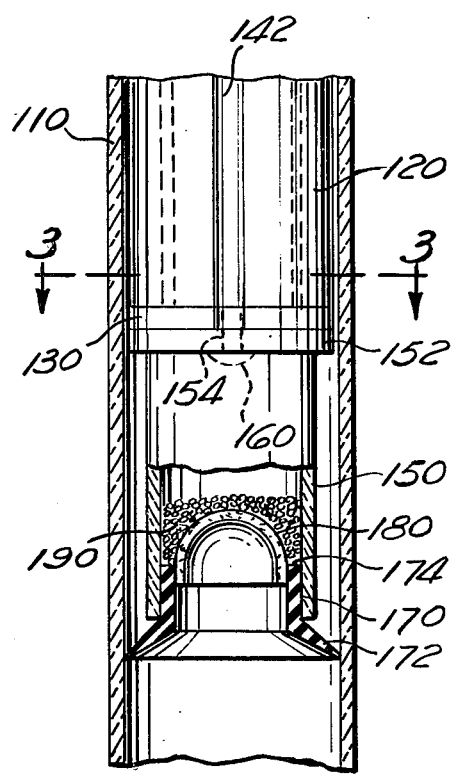
FIG. 2 is a cross-sectional view showing in detail the structure of the reaction chamber, the plunger filter including the filter, the movable seal, and the bottom of the multiple reagent chamber, in which the respective chambers are so configured and constructed so as selectively to be in fluid communication with the reaction chamber.

As best shown in FIG. 3, each of the chambers is provided with a port, Ports 132, 134, 136 and 138 coinciding respectively with Chambers A, B, C and D. As will be described in greater detail hereinafter, these ports permit selective fluid communication between the respective reagent chambers and the reaction chamber which will be described hereinafter.

A notch or indent 142 selectively receives a protuberance 140 to index the reagent chambers such that the passages are, respectively, in fluid communication with the reaction vessel. The protuberance 140 is formed on the cap of the reaction vessel defined by a cylindrical wall 150 and a cap 152. The reagent chamber assembly is rotatable relative to the reaction vessel assembly and the protuberance 140 fits, respectively, into indentations 142, 144, 146 and 148, shown best in FIG. 3, to index the ports 132, 134, 136 and 138 of the respective reagent chambers A, B, C and D.

The means forming the reaction vessel comprise a cylindrical wall 150, means forming a closure 152 which substantially closes the distal end of the reaction chamber, a seal 170 comprises a skirt 172 which extends outwardly forming a movable, fluid-tight seal, each forming the reaction chamber and the cylindrical tube 110, and also comprises an insert sleeve 174 which is in fluid-tight relationship in the interior of the reaction chamber, thus forming a fluid-tight, movable seal between the plunger filter assembly and the cylindrical container tube. The reaction chamber is closed by a dome-shaped filter which is inside and closes the proximal end of the reaction chamber to passages of material in and out of said proximal end except for fluids and particles which can pass through the filter. The filter 180 retains within the reaction chamber a multiplicity of immunologically reactive beads which, in use, by the selective immunologically active constituents of the fluid immunoassay, the immunologically active beads having pore surfaces treated with an immunologically active constituents and being too large to pass through the filter 180.

In summary, then, this system may be described as a cylindrical container tube (110) having an open end and a closed end and a plunger filter assembly received in the open end of the container tube with means slidable in the container tube. The plunger filter assembly comprises means (150) forming a cylindrical reaction chamber which is open at the proximal end. A movable seal (170, 172, 174) is secured at the proximal end of the reaction chamber and is movable with respect to the interior walls of the container tube (110) and forms a substantially fluid-tight movable seal between the proximal end of the plunger filter and the container tube. A dome-shaped filter (180) is secured to the sealing means (170-174), in the preferred embodiment, inside and closing the proximal end of the reaction chamber to passage of material in and out of said proximal end except for fluids and particles which can pass through the filter (180). Immunologically reactive beads (190) are contained in the reaction chamber which, in use, bind selective immunologically active constituents of the fluid to be assayed. The plunger filter assembly also includes means (120-128) forming plural reagent chambers (A-D), said means being secured adjacent the closure (152) to the reaction chamber for movement relative to said closure. In the preferred form, the movement is relative rotatable movement, the means forming the plural reagent chambers and the closure means for the reaction chamber being rotatably secured together as by a pin 160 or other rotatable fastening means. The chamber forming means also forms a proximal end to the chambers having ports (132-138) in each of the respective chambers. Means (140-148) are provided for selectively aligning the respective ports in said reagent chambers with the port in the closure to the reaction chamber for permitting fluid communication and air outlets between the reaction chamber and, selectively, the respective reagent chambers by rotating the means for reagent chambers.

It will be understood that within the teachings of this invention, considerable variance may be permitted as to individual elements, so long as the overall combination and function of the combination is retained. For example, a variety of fastening means or securing means may be provided to permit relative movement of the ports between the respective reagent chambers and the reaction chamber. Rotatable movement is, of course, the most efficient in terms of space and convenient for manufacture but is not the only possible form of movement contemplated.

A variety of means for permitting indexing of the plural chambers with the reaction chamber may be provided. In the particular embodiment shown, the protuberance and the indents 140 and 142–148 respectively, are convenient means. Other forms of indents and other forms of protuberances, for example, a protuberance extending upwardly from the closure 152 into indents formed in the bottom of the means closing the reagent chambers 120 may be provided. Resilient means for aligning the ports of the respective reagent chambers may also include various resilient latching and indexing means not specifically disclosed without departing from the scope of the invention. The essential feature, in this particular respect, is that means are provided to permit alignment of the ports in the respective reagent chambers with the port in the reaction chamber to selectively permit reagents to pass through the aligned ports from the reagent chamber to the reaction chamber.

The foregoing are simply illustrative examples of the variations which may within the skill of the art, for convenience in manufacture and use, may be made without departing from the invention as defined in the claims which are appended hereto.

The basic immunological reaction, in an exemplary form, is described as follows. An antibody with specificity for a "test antigen" is covalently coupled to the beads. The beads, to which the antibody is coupled, are retained in the plunger-filter. These "antibodybeads" are resuspended, during use, within the plunger-filter in the presence of the biological fluids or other fluids to be assayed for the "test antigen". At the same time, or subsequently, the antibody-beads are incubated in a solution containing a "second antibody-enzyme". This second antibody-enzyme also has specificity for the test antigen and, in addition, is covalently coupled to an enzyme. If the test antigen is present in the assayed biological or other fluid, it will bind to both antibodies. Some of the test antigen will be bound simultaneously to the antibody bead and to the second antibody enzyme. In this way, the second antibody enzyme is bound to the beads and is retained on the beads through the highly specific immunological reaction. The antibody beads, with the antigen and the antibody-enzyme bound thereto, are then washed by vacuum suction applied at the filter base, by introducing the wash solution into the plunger-filter and pulling the plunger-filter up, as shown in the Figures, in the cylindrical container tube 110 to force the wash solution through the filter. Finally, the beads are re-suspended in a "developing substrate solution". The enzyme, coupled to the second antibody, alters the substrate and results in a color change, or some other detectable phenomena. The developing solution will, in the colorimetric method, change color visibly, or in the ultraviolet or infrared range, and this color change can be detected either visually or by use of appropriate ultraviolet or infrared photometric instruments. The change, per se, constitutes a quantitative indication of the presence of the test antigen. The amount of the change in the developing solution, e.g. the intensity of the color, the intensity of the radiation, etc., is a quantitative indicator of the amount of the test antigen in the assayed fluid.

It will be noted that the above description is an adaptation of a known antibody enzyme-linked immunoassay to the plunger-filter system of this invention, and is given merely as an example.

By having a "first antibody" present on suspendable small beads, rather than on a flat surface, a very much greater random interface is rapidly achieved between the antibody and the test antigen. Since the antibody will more frequently "see" the test antigen, the reaction time is much faster and the reaction runs much closer to completion. It has been shown that when the beads are kept in suspension during incubation, an incubation time of under 15 minutes can result in immunoassays with at least nanogram/milliliter sensitivity. This compares with immunoassays which require several hours if the first antibody is attached only to a flat surface.

Another important advantage is that centrifugations are avoided entirely. The liquid can be evacuated from the plunger by suction, with the antibody beads being retained within the plunger filter.

Filter plungers are currently manufactured for a single clinical use, the collection of serum or plasma from patient blood. When blood is centrifuged, the blood cells are spun down to the bottom of the tube, leaving the plasma-serum at the top. Filter plungers are inserted into the tubes, stopping short of the blood cells, enabling serum-plasma to pass into the plunger. The filter prevents clots and other particulate debris from entering the plunger. None of the currently manufactured filter-plungers are, however, suitable for assay according to this invention. To achieve an assay of high sensitivity, short reaction time, and low color background, the conditions of bead size and bead porosity, filter pore size, plunger geometry, and fluid density during the antibody-antigen reaction are very significant. In addition, the present invention permits direct immunoassay of whole blood, as opposed to conventionally assayed serum or plasma. These various facets of the invention are now discussed.

Using carefully defined filter and bead dimensions, it is possible to assay anti-coagulated whole blood. This eliminates a time-consuming chore of preparing plasma or serum from blood. To assay whole blood, plungers are fitted with filters which retain particles of 15-microns or greater. Since normal blood cells are all smaller than 15 microns in diameter, they can pass freely through the filter into the plunger-filter which defines the reaction chamber to begin the antibody-antigen reaction, then pass freely out through the filter at the end of the reaction, leaving the antibody beads behind. Hemolysis is minimal. The antibody beads are chosen to be larger than 20 microns in diameter so that they are retained by and do not clog the filter. It has been found that polydextran beads of 20–35 micron size are quite suitable for this purpose. Thus, with a 20-micron filter, it is important that beads with the immunologically binding constituent thereon have a size in the range of about 20–35 microns.

To run a reaction on whole blood optimally, a filter with a pore size just large enough to let the blood cells pass freely, but small enough to retain the beads which are not so small as to clog the filter but themselves are as small as possible to better remain in the suspension during incubations, is required. Less than optimal results may, of course, be achieved using smaller beads even though some modest clogging may result or larger beads which will tend to settle, if time, stirring, shaking, or other accommodation is made to overcome these particular disadvantages.

The beads should have a small pore size, i.e. the beads are porous, but not so porous that they present a large internal surface. The beads should be porous at the surface to assure that all or substantially all of the coupling immunological reagent, e.g. the antibody, is present on the outer surface of the beads. Typically, the pore sizes of the beads should be less than 10,000 millimicrons. This speeds the antigen-antibody reaction, since the test antigen does not have to migrate into the beads to interface with the antibody bound to the beads. In addition, small pore size prevents the second antibody-enzyme from entering the beads. If the latter occurs, the second antibody-enzyme will be carried over nonspecifically during the wash steps, resulting in an unwanted higher background during development. It has been clearly demonstrated that the low porosity beads are of great value in the assay procedure of this invention. Highly porous beads, e.g., dextran and polacrylamide, give very high backgrounds, whereas small-pore dextran or polyacrylamide beads give essentially zero background.

The first stage incubation, during which the antibody beads are reacted with the test antigen, proceeds faster if the beads are evenly dispersed in the incubation fluid. It is, therefore, highly desirable to avoid the settling of the beads. This can be achieved by rocking, stirring or agitating the plunger-filter assemblies during the reaction. This may be done by hand or automatically by appropriate rocking equipment. However, according to this invention even this inconvenience is avoided by adding a carrier or densifying substance to the fluid. Certain carrier substances are of sufficient density and possess appropriate charge properties to prevent the settling of antibody beads. Carriers such as Ficoll-Hypaque and glycerol are suitable for many assays. Other densifying and thickening carriers may also be used. It should be noted that in assays of whole blood there is little or no need of any additional carrier since the density of the blood itself is usually sufficiently high to prevent settling or at least to provide for very slow settling of the beads.

The foregoing technique is broadly applicable to biological fluids of virtually any type. The technique is also applicable to other fluids, and to other types of immunoassays, quite obviously. For example, if it is desired to assay exudates, secretions, fecal materials, etc., the technique is very easily and effectively adapted to such an approach. A soft, inert, easily compressible material, such as silicone foam or a cellulose swab, etc., mounted on a detachable plastic or cardboard "swab" stick, is wiped on the area to be tested, such as the pharynx, rectum, and the stick is then detached from the sponge ball, which is dropped into an appropriately sized container tube. The plunger, containing antibody beads, is then pressed against the test tube as far as possible, bearing down forcefully on a sponge ball. With fluid covering the sponge ball, the sponge ball may be "pumped" a number of times. When strongly compressed one time or repeatedly in a pumping approach, the biological fluid is expressed out of the ball and then is carried with the solution through the filter into the plunger-filter assembly. When assays are run on these types of materials rather than whole blood, the filter porosity can be very much smaller than 20 microns, and the bead size may be commensurately smaller, thus resulting in a slower bead settling. Generally, the bead size will be approximately 30% greater than the pore diameter of the filter, although the particular ratio is not highly critical.

The technique of this invention may, as earlier indicated, be applied to virtually any type of immunoassay. For example, it may be used to carry out immunocompetition assays, such as the assay of digoxin.

While antibody beads have been used for some time in immunological assays (see, for example, Richman, Douglas D., et al, "The Binding of Staphylococcal Protein A By the Sera of Different Animal Species", *Journal of Immunology,* Vol. 128, No. 5, 1982), the plunger-filter construction and technique described hereinbefore is believed to be entirely novel and to be highly advantageous over all known prior techniques and apparatus. The plunger-filter apparatus of this invention is entirely new and its use as systems for assays not involving radioactivity or simply to eliminate more steps is novel. Particularly, its usefulness in reducing reaction time by hours is a new concept and approach in the art. As described above, the existing plunger technology as well as reagent and sample handling, have been greatly improved to achieve the particular ends of high sensitivity, rapid reaction time, convenience, low-cost, and low background development.

The invention, as described hereinbefore, includes a number of advantageous features. First is the use of enzyme-linked assay in a plunger-filter system, which provides extremely high sensitivity coupled with low cost and high efficiency and a short time delay. The deliberate use of antibody-beads rather than antibody on a flat phase to increase the reaction surface area accelerates reaction time. Combining the use of beads with the plunger-filter system further reduces the time in running an assay. The balancing of the necessary properties of the filter and the beads to reduce bead settling during incubation of the assay very much shorten incubation time with great and unexpected advantages over the prior art. The deliberate use of small-pore beads to prevent the entrance of a developing reagent, e.g. a second antibody-enzyme, and to hasten encounters between the antigen and the developing reagent, has also proven to be a very great advance, reducing time and increasing sensitivity of the assay. The design of the plunger-filter to eliminate fluid and cell retention is also regarded as a very important feature of the invention. Effective wash suction cannot be applied to the plunger-filter with the prior art device.

The features include the use of a high density fluid, such as glycerol, to keep the beads in suspension. The reducable cross-linking enzyme on the second antibody-enzyme conjugate is also highly advantageous so that the enzyme can be liberated from the beads and color development, or other development reaction, can proceed in a clean tube, is also significant. The use of nonionic detergents and anti-foam agents is a further advantage in the wash solutions to prevent high background in the color development.

A very distinct and important advantage of the present invention is that it can be used to assay whole, anticoagulated, blood and carrier solutions, as well as biological materials. Another advantage is that the technique and apparatus of this invention can be used to run virtually any kind of immunological assay.

In use, the sample to be assayed is placed in the bottom end, as shown in figures, of the container tube 110. Obviously, the container tube may be formed such as to permit drawing the sample through syringe action directly into the bottom of the tube, or may simply be poured or otherwise introduced into the container. The plunger filter assembly is pressed downwardly, as shown in the figures, forcing the sample up through the filter 180 into contact with the beads 190. Immediately thereafter the port in reagent Chamber A is indexed to the reaction chamber thereby allowing the contents in Chamber A to enter the reaction chamber. After a suitable incubation, the plunger filter assembly is moved upwardly, thus forcing the sample downwardly leaving the beads. The beads may be washed by indexing the port in reagent Chamber B with a port in the reaction chamber. After several washing actions, as, for example, by shaking, rocking or simply delay, the material filter assembly is moved upward again forcing the wash solution into the container 110. The reagent chamber means is turned such that Chamber C port is aligned with the port in the reaction chamber thereby emptying the contents of Chamber B into the reaction chamber. This is repeated again with respect to Chamber D which, typically, would contain the developer.

By this technique and using the invention, all of the reagents necessary for completing a total assay are contained in one container which may be shipped as an article of commerce, reagents, beads and all. Only the sampling added in the procedures described above are implemented.

It will be apparent that means may be provided for forming any number of reagent chambers. Typically, four is a convenient number because of the number of reagents often involved. However, two, three, or even up to six or eight reagent chambers may conveniently be provided. In the particular embodiment shown, which is a preferred embodiment because of its simplicity, the means forming the plural reagent chambers is also cylindrical and is adapted to fit down into the container cylinder; however, this is not necessary. For example, enlarged means forming plural reagent chambers could be formed which would be larger than the container cylinder in which only the bottom part of the filter plunger assembly would be slidably received, the sliding fluid-tight relationship between the filter plunger assembly and the container cylinder being maintained by the sealer described. Another alternative design could be to line the plural reagent chambers horizontally, pulling the reaction chamber sequentially into contact with each upper chamber along a linear track, rather than operating in a rotating chamber format. Obviously, other variations, within the concept and teachings of this invention, could easily be made without departing from the scope and content of the invention as described herein and as defined in the claims which are appended hereto.

INDUSTRIAL APPLICATION

The apparatus and methods of this invention are adapted for use in industrial, research, scientific and clinical laboratories generally, wherever any type of immunological assay is run. The invention provides highly efficient, high sensitivity, low cost immunoassay techniques and apparatus.

What is claimed is:

1. An immunoassay apparatus comprising:
    a cylindrical container tube having an open end and a closed end; and
    a plunger filter assembly received in the open end of the container tube and being slidable in the container tube the plunger filter assembly comprising means forming a reaction chamber open at the proximal end, a movable seal secured at the proximal end of the reaction chamber, closure means substantially closing the distal end of the reaction chamber and forming an off-center port therethrough, the seal in said proximal end being movable with respect to the interior walls of the container tube and forming a substantially fluid tight movable seal between the proximal end of the plunger filter and the container tube, a dome-shaped filter inside and closing the proximal end of the reaction chamber to the passage of material in and out of said proximal end except for fluids and particles which can pass through the filter, and immunologically reactive beads in said raction chamber which, in use, bind selected immunologically active constituents, of the fluid to be assayed, the immunologically active beads having porous surfaces treated with an immunologically active constituent and being too large to pass through the filter, and means forming plural reagent chambers secured adjacent said closure to said reaction chamber for movement relative to said closure, said chamber forming means forming a proximal end having a port therethrough and means for selectively aligning the respective ports in said reagent chambers with the port in the closure to the reaction chamber for fluid communication therebetween.

2. The apparatus of claim 1 wherein the filter includes passages therethrough approximately one-half the diameter of the beads.

3. The apparatus of claim 1 or claim 2 wherein the seal comprises a skirt extending circumferentially around the plunger filter tube into movable sealing contact with the internal wall of the container tube and a sleeve securely received inside the plunger filter tube, the top of the sleeve being so constructed and arranged as to form a generally flat annular top surface with intersects with the internal wall of the plunger filter tube at an angle of not more than 90°.

4. The apparatus of claim 4 wherein the angle is approximately 90°.

5. The apparatus of claims 1, 2, 3 or 4 wherein the beads are of small enough porosity to cause all immunological reactions to occur on the outside of the beads.

6. The apparatus of claims 1, 2 or wherein the means forming plural reagent chambers is rotatable relative the closure.

7. The apparatus of claims 1, 2 or 3 wherein the means forming plural reagent chambers forms at least four reagent chambers, is cylindrically configured, is adapted to move reciprocally in said cylindrical container tube and is rotatably secured to the distal end of the means forming the reaction chamber, the ports in said reagent chambers being selectively alignable with the port in the closure to the reaction chamber.

* * * * *